US00PP35494P2

(12) United States Plant Patent
Barends

(10) Patent No.: US PP35,494 P2
(45) Date of Patent: Nov. 21, 2023

(54) ***OSTEOSPERMUM* PLANT NAMED 'DOOSTMARKAR'**

(50) Latin Name: *Osteospermum ecklonis*
Varietal Denomination: Doostmarkar

(71) Applicant: DUMMEN GROUP B.V., De Lier (NL)

(72) Inventor: Eveline Desiree Barends, De Lier (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 18/078,397

(22) Filed: Dec. 9, 2022

(51) Int. Cl.
*A01H 5/02* (2018.01)
*A01H 6/14* (2018.01)

(52) U.S. Cl.
USPC ..... Plt./360

(58) Field of Classification Search
USPC ..... Plt./263.1, 360
See application file for complete search history.

(56) References Cited

PUBLICATIONS

Dummen Orange 2022-2023 Annuals catalog. https://na.dummenorange.com/app/pdfcatalogs/detail.web?catalogId=173.2 pgs. (Year: 2022).*
Galema's Greenhouse 2020 spring catalog. https://www.galemas.com/GGSpring2020catalogweb.pdf. 4 pgs. (Year: 2020).*

* cited by examiner

*Primary Examiner* — Karen M Redden
(74) *Attorney, Agent, or Firm* — C. Anne Whealy

(57) ABSTRACT

A new and distinct cultivar of *Osteospermum* plant named 'Doostmarkar', characterized by its compact, broadly upright, uniform and mounding plant habit; moderately vigorous growth habit; freely and uniformly branching habit; freely and early flowering habit; large single-type inflorescences with reddish purple-colored ray florets; and good garden performance.

1 Drawing Sheet

Botanical designation: *Osteospermum ecklonis.*
Cultivar denomination: 'DOOSTMARKAR'.

BACKGROUND OF THE INVENTION

The present invention relates to a new and distinct cultivar of *Osteospermum* plant, botanically known as *Osteospermum ecklonis*, and hereinafter referred to by the name 'Doostmarkar'.

The new *Osteospermum* plant is a product of a planned breeding program conducted by the Inventor in Puerto Lumbreras, Spain and De Lier, The Netherlands. The objective of the program is to create and develop new compact *Osteospermum* plants that are freely and uniformly branching with numerous large inflorescences with unique and attractive ray and disc floret coloration.

The new *Osteospermum* plant originated from a cross-pollination by the Inventor during the winter of 2014 of a proprietary selection of *Osteospermum ecklonis* identified as code number QQ12-000005-001, not patented, as the female, or seed, parent with *Osteospermum ecklonis* 'Summertime Kardinal, not patented, as the male, or seed, parent. The new *Osteospermum* plant was discovered and selected by the Inventor as a single flowering plant within the progeny of the stated cross-pollination in a controlled greenhouse environment in De Lier, The Netherlands in July, 2015.

Asexual reproduction of the new *Osteospermum* plant by terminal vegetative cuttings in a controlled greenhouse environment in De Lier, The Netherlands since August, 2015 has shown that the unique features of this new *Osteospermum* plant are stable and reproduced true to type in successive generations.

SUMMARY OF THE INVENTION

Plants of the new *Osteospermum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Doostmarkar'. These characteristics in combination distinguish 'Doostmarkar' as a new and distinct *Osteospermum* plant:

1. Compact, broadly upright, uniform and mounding plant habit.
2. Moderately vigorous growth habit.
3. Freely and uniformly branching habit.
4. Freely and early flowering habit.
5. Large single-type inflorescences with reddish purple-colored ray florets.
6. Good garden performance.

Plants of the new *Osteospermum* differ primarily from plants of the female parent selection in ray floret color as ray florets of plants of the new *Osteospermum* are reddish purple in color whereas ray florets of plants of the female parent selection are pink in color.

Plants of the new *Osteospermum* differ primarily from plants of the male parent, 'Summertime Kardinal', in branching habit as plants of the new *Osteospermum* are more freely branching than plants of 'Summertime Kardinal'.

Plants of the new *Osteospermum* can be compared to plants of the *Osteospermum ecklonis* 'Margarita Cool Purple', not patented. In side-by-side comparisons, plants of the new *Osteospermum* differ primarily from plants of 'Margarita Cool Purple' in the following characteristics:

1. Plants of the new *Osteospermum* are taller than plants of 'Margarita Cool Purple'.
2. Leaves of plants of the new *Osteospermum* are larger than leaves of plants of 'Margarita Cool Purple'.
3. Ray florets of plants of the new *Osteospermum* are broader than ray florets of plants of 'Margarita Cool Purple'.
4. Peduncles of plants of the new *Osteospermum* are stronger than peduncles of plants of 'Margarita Cool Purple'.

BRIEF DESCRIPTION OF THE PHOTOGRAPH

The accompanying photograph illustrates the overall appearance of the new *Osteospermum* plant showing the colors as true as it is reasonably possible to obtain in colored reproductions of this type. Colors in the photograph may differ slightly from the color values cited in the detailed botanical description which accurately describe the colors of the new *Osteospermum* plant. The photograph is a side perspective view of a typical flowering plant of 'Doostmarkar' grown in a container.

DETAILED BOTANICAL DESCRIPTION

The aforementioned photograph, following observations and measurements describe plants grown during the summer and autumn in 10.5-cm containers in a glass-covered greenhouse in De Lier, The Netherlands and under cultural practices typical of commercial *Osteospermum* production. During the production of the plants, day temperatures ranged from 18° C. to 30° C. and night temperatures ranged from 14° C. to 18° C. Plants were pinched five weeks after sticking unrooted cuttings; plants were 13 weeks old when the photograph was taken and 15 weeks old when the description was taken. In the following description, color references are made to The Royal Horticultural Society Colour Chart, Fifth Edition, except where general terms of ordinary dictionary significance are used.

Botanical classification: *Osteospermurn ecklonis 'Doostmarkar'*.

Parentage:

*Female, or seed, parent.*—Proprietary selection of *Osteospermum ecklonis* identified as code number QQ12-000005-001, not patented.

*Male, or pollen, parent.*—*Osteospermum ecklonis* 'Summertime Kardinal', not patented.

Propagation:

*Type.*—Terminal vegetative cuttings.

*Time to initiate roots, summer.*—About 18 days at temperatures about 22° C. to 30° C.

*Time to initiate roots, winter.*—About 21 days at temperatures about 22° C. to 30° C.

*Time to produce a rooted cutting, summer.*—About 25 days at temperatures about 22° C. to 30° C.

*Time to produce a rooted cutting, winter.*—About 28 days at temperatures about 20° C. to 25° C.

*Root description.*—Medium in thickness, fibrous; typically whitish grey in color, actual color of the roots is dependent on substrate composition, water quality, fertilizers, substrate temperature and age of roots.

*Rooting habit.*—Moderately freely branching; medium density.

Plant description:

*Plant form and growth habit.*—Compact, broadly upright, uniform and mounding plant habit; freely branching habit, dense and bushy growth habit; moderately vigorous growth habit and moderate growth rate.

*Plant height, soil level to top of foliar plane.*—About 34 cm.

*Plant height, soil level to top of floral plane.*—About 35 cm.

*Plant diameter.*—About 32 cm.

*Lateral branches.*—Quantity per plant: Freely branching habit, about five primary lateral branches each with about four to six secondary lateral branches developing per plant; pinching enhances lateral branch development. Length: About 21.5 cm to 24 cm. Diameter: About 6 mm. Internode length: About 1.2 cm. Strength: Moderately strong. Texture and luster: Smooth, glabrous; semi-glossy. Color, developing: Close to 144C to 144D. Color, developed: Close to 144C.

*Leaf description.*—Arrangement: Opposite, simple. Length: About 8 cm. Width: About 4.5 cm. Shape: Spatulate. Apex: Acute. Base: Attenuate. Margin: Dentate and lobing; sinuses are medium in depth and divergent. Texture and luster, upper surface: Pubescent; leathery; slightly glossy. Texture and luster, lower surface: Smooth, glabrous; leathery; slightly dull. Venation pattern: Pinnate. Color: Developing leaves, upper surface: Close to N137A. Developing leaves, lower surface: Close to 138B. Fully expanded leaves, upper surface: Close to N137A; venation, close to 137B. Fully expanded leaves, lower surface: Close to 138B; venation, close to 138B.

*Petioles.*—Length: About 3.5 cm to 4.5 cm. Diameter: About 4 mm. Texture, upper and lower surfaces: Smooth, glabrous; slightly glossy. Strength: Moderately strong. Color, upper and lower surfaces: Close to 144B.

Inflorescence description:

*Appearance and aspect.*—Terminal and axillary inflorescences; inflorescences positioned beyond the foliar plane on strong peduncles and face mostly upright to outwardly; single-type inflorescence form with lanceolate-shaped ray florets and tubular disc florets; ray and disc florets developing acropetally on a capitulum.

*Flowering habit.*—Freely flowering habit; about 20 to 40 inflorescence buds and open inflorescences per plant.

*Fragrance.*—None detected.

*Flowering response.*—In The Netherlands, plants of the new *Osteospermum* flower continuously from spring until first frost in the autumn; early flowering habit, plants begin flowering about 50 to 60 days after rooting cuttings.

*Inflorescence longevity.*—Inflorescences last about two weeks on the plant; inflorescences not persistent.

*Inflorescence buds.*—Height: About 1.4 cm, depending on stage of development. Diameter: About 1 cm, depending on stage of development. Shape: Flattened globular. Texture and luster: Smooth, glabrous; semi-glossy. Color: Close to 137B and 144C.

*Inflorescence size.*—Diameter: About 6.4 cm. Depth (height): About 2.8 cm. Disc diameter: About 1 cm. Receptacle diameter: About 7 mm. Receptacle height: About 3 mm. Receptacle color: Close to 137C.

*Ray florets.*—Quantity per inflorescence and arrangement: About 14 to 16 arranged in a single whorl. Length: About 3.5 cm. Width: About 1.4 cm. Shape: Lanceolate. Apex: Obtuse or slightly emarginate. Base: Cuneate. Margin: Entire; not undulate. Aspect: Mostly flat. Texture and luster, upper and lower surfaces: Smooth, glabrous; matte. Color: When opening, upper surface: Close to N78A. When opening, lower surface: Close to 79A. Fully opened, upper surface: Close to N78A; venation, close to 79A; color does not change with subsequent development. Fully opened, lower surface: Close to N78B; venation, close to N78B; color becoming closer to 79A with subsequent development.

*Disc florets.*—Quantity per inflorescence and arrangement: About 50 arranged in about seven to nine whorls. Length: About 5 mm. Diameter: About 1 mm. Shape: Tubular with five obtuse apices. Aspect: Upright. Texture and luster: Smooth, glabrous; matte. Color: When developing, inner surface: Close to N79A. When developing, outer surface: Close to 79A. Fully developed, inner surface: Close to 91B; venation, close to 79A; color becoming closer to 79B with subsequent development. Fully developed, outer surface: Close to 79A; venation, close to 91B; color becoming closer to 79B with subsequent development.

*Phyllaries.*—Quantity per inflorescence and arrangement: About 21 arranged in about one to two whorls. Length: About 9 mm. Width: About 1 mm. Shape: Ovate. Apex: Acute. Base: Cuneate. Margin: Entire. Texture and luster, upper and lower surfaces: Smooth, glabrous; matte. Color, upper and lower surfaces: Close to 137A.

*Peduncles.*—Length: About 9 cm to 13 cm. Diameter: About 2 mm. Strength: Strong. Aspect: Mostly upright to outwardly slanting. Texture and luster: Smooth, glabrous; semi-glossy. Color: Close to 144A.

*Reproductive organs.*—Androecium: Present on disc florets only. Filament length: About 4 mm. Filament color: Close to 17A. Anther size: About 1.5 mm by 9 mm. Anther shape: Narrowly elliptic. Anther color: Close to 6A. Pollen amount: Moderate. Pollen color: Close to 17B. Gynoecium: Present on both ray and disc florets. Pistil length: About 3 mm. Stigma shape: Bi-parted. Stigma color: Close to 7A. Style length: About 3 mm. Style color: Close to 2A. Ovary color: Close to 145C.

*Fruits and seeds.*—To date, fruit and seed development has not been observed on plants of the new *Osteospermum.*

Pathogen & pest resistance: To date, plants of the new *Osteospermum* have not been observed to be resistant to pathogens and pests common to *Osteospermum* plants.

Garden performance: Plants of the new *Osteospermum* have been observed to have good garden performance and to tolerate rain, wind and temperatures ranging from about 5° C. to about 35° C.

It is claimed:

1. A new and distinct *Osteospermum* plant named 'Doostmarkar' as illustrated and described.

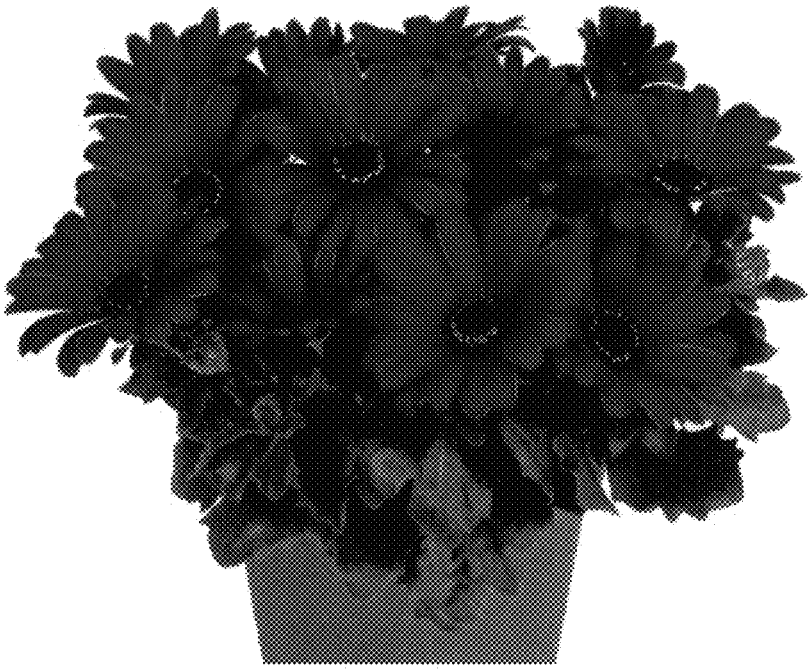

* * * * *